US006616922B2

(12) United States Patent
Taylor et al.

(10) Patent No.: US 6,616,922 B2
(45) Date of Patent: Sep. 9, 2003

(54) ANTIBACTERIAL COMPOSITIONS

(75) Inventors: Timothy J. Taylor, Phoenix, AZ (US); Priscilla S. Fox, Phoenix, AZ (US); E. Phil Seitz, Scottsdale, AZ (US); Michael D. Slayton, Cave Creek, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 09/818,366

(22) Filed: Mar. 27, 2001

(65) Prior Publication Data

US 2003/0022941 A1 Jan. 30, 2003

(51) Int. Cl.$^7$ ............................. A61K 7/50; A61K 7/40
(52) U.S. Cl. ............... 424/70.28; 424/70.1; 424/70.27; 424/400; 424/404
(58) Field of Search ..................... 514/358; 424/70.28, 424/70.1, 70.27, 400, 404

(56) References Cited

U.S. PATENT DOCUMENTS

| | | | |
|---|---|---|---|
| 4,062,976 A | 12/1977 | Michaels | 424/319 |
| 4,075,350 A | 2/1978 | Michaels | 424/316 |
| 4,107,328 A | 8/1978 | Michaels | 424/316 |
| 4,145,436 A | 3/1979 | Michaels | 424/273 R |
| 5,244,652 A | 9/1993 | Michaels | 424/54 |
| 5,314,917 A | 5/1994 | Michaels et al. | 514/556 |
| 5,389,676 A | 2/1995 | Michaels | 514/556 |
| 5,635,462 A | 6/1997 | Fendler et al. | 510/131 |
| 5,798,329 A | 8/1998 | Taylor et al. | 510/384 |
| 5,908,854 A * | 6/1999 | McCue et al. | 514/358 |
| 5,929,016 A | 7/1999 | Harrison | 510/384 |
| 5,968,539 A | 10/1999 | Beerse et al. | 424/405 |
| 6,106,851 A | 8/2000 | Beerse et al. | 424/401 |
| 6,107,261 A * | 8/2000 | Taylor et al. | 510/131 |
| 6,113,933 A | 9/2000 | Beerse et al. | 424/404 |
| 6,117,828 A * | 9/2000 | Puvvada et al. | 510/124 |
| 6,136,771 A * | 10/2000 | Taylor et al. | 510/338 |
| 6,204,230 B1 * | 3/2001 | Taylor et al. | 510/131 |
| 6,451,748 B1 * | 9/2002 | Taylor et al. | 510/131 |

FOREIGN PATENT DOCUMENTS

| | | | |
|---|---|---|---|
| EP | 0 505 935 | 9/1992 | C11D/3/48 |
| EP | 0 651 048 | 5/1995 | C11D/1/835 |
| EP | 0882446 A1 * | 12/1998 | |
| EP | 0 882 446 | 12/1998 | |
| WO | WO 92/16182 | 10/1992 | |
| WO | WO 92/16201 | 10/1992 | A61K/31/205 |
| WO | WO 95/09605 | 4/1995 | A61K/7/50 |
| WO | WO 95/32705 | 12/1995 | A61K/7/50 |
| WO | WO 96/06152 | 2/1996 | C11D/3/00 |
| WO | WO 97/15647 | 5/1997 | C11D/1/62 |
| WO | WO 97/46218 | 12/1997 | A61K/7/48 |
| WO | WO 98/01110 | 1/1998 | A61K/7/48 |
| WO | WO 98/55096 | 12/1998 | A61K/7/50 |
| WO | WO 99/19438 * | 4/1999 | |

OTHER PUBLICATIONS

Allawala et al., *Journal of the American Pharmaceutical Association*, vol. XIII, No. 5, pp. 267–275 (1953).
Mitchell, *J. Pharm. Pharmacol.* 16, pp. 533–537 (1964).

* cited by examiner

*Primary Examiner*—Thurman K. Page
*Assistant Examiner*—Rachel M. Bennett
(74) *Attorney, Agent, or Firm*—Marshall, Gerstein & Borun

(57) ABSTRACT

Antibacterial compositions having enhanced antibacterial effectiveness are disclosed. The antibacterial compositions contain an antibacterial agent, an alkamine oxide, a nonionic and/or cationic cosurfactant, an optional polymeric thickener, and water.

37 Claims, No Drawings

ANTIBACTERIAL COMPOSITIONS

FIELD OF THE INVENTION

The present invention is directed to antibacterial compositions, like personal care compositions, having improved antibacterial effectiveness and excellent esthetic properties. More particularly, the present invention is directed to antibacterial compositions comprising an antibacterial agent, an alkamine oxide, a cosurfactant, and an optional polymeric thickener. Preferred compositions have a pH of about 5.5 to about 7.5. A present composition provides a substantial reduction, e.g., greater than 99%, in Gram positive and Gram negative bacterial populations within one minute.

BACKGROUND OF THE INVENTION

Antibacterial personal care compositions are known in the art. Especially useful are antibacterial cleansing compositions, which typically are used to cleanse the skin and to destroy bacteria and other microorganisms present on the skin, especially the hands, arms, and face of the user.

Antibacterial compositions are used, for example, in the health care industry, food service industry, meat processing industry, and in the private sector by individual consumers. The widespread use of antibacterial compositions indicates the importance consumers place on controlling bacteria and other microorganism populations on skin. It is important, however, that antibacterial compositions provide a substantial and broad spectrum reduction in microorganism populations quickly and without problems associated with toxicity and skin irritation.

In particular, antibacterial cleansing compositions typically contain an active antibacterial agent, a surfactant, and various other ingredients, for example, dyes, fragrances, pH adjusters, thickeners, skin conditioners, and the like, in an aqueous carrier. Several different classes of antibacterial agents have been used in antibacterial cleansing compositions. Examples of antibacterial agents include bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and triclosan (i.e., 2,4,4'-trichloro-2'hydroxy-diphenylether). Present-day antimicrobial compositions based on such antibacterial agents exhibit a wide range of antibacterial activity, ranging from low to high, depending on the microorganism to be controlled and the particular antibacterial composition.

Most commercial antibacterial compositions, however, generally offer a low to moderate antibacterial activity. Antibacterial activity is assessed against a broad spectrum of microorganisms, including both Gram positive and Gram negative microorganisms. The log reduction, or alternatively the percent reduction, in bacterial populations provided by the antibacterial composition correlates to antibacterial activity. A log reduction of 3–5 is most preferred, a 1–3 reduction is preferred, whereas a log reduction of less than 1 is least preferred, for a particular contact time, generally ranging from 15 seconds to 5 minutes. Thus, a highly preferred antibacterial composition exhibits a 3–5 log reduction against a broad spectrum of microorganisms in a short contact time. Prior disclosures illustrate attempts to provide such antibacterial compositions, which, to date, do not provide the rapid, broad range control of microorganisms desired by consumers.

It should be noted that high log reductions have been achieved at pH values of 4 and 9, but such log reductions are attributed at least in part to these relatively extreme pH values. Compositions having such pH values can irritate the skin or damage other surfaces, and, therefore, typically are avoided. It has been difficult to achieve a high log reduction using an antibacterial composition having a neutral pH of about 5.5 to about 7.5, and especially about 6 to about 7.3. Antibacterial compositions having a near neutral pH are disclosed in U.S. Pat. Nos. 6,107,261 and 6,136,771.

In addition to an antibacterial agent, antibacterial personal care compositions typically contain an anionic surfactant for cleansing and foam generation, skin conditioning agents for cosmetic effects, and dyes, perfumes, and optional thickening agents, such as clays, polymers, or colloids, for esthetic effects. The most common antibacterial agents are selected from the classes of phenolic compounds, carbanalide compounds, lower alcohols, and quaternary ammonium compounds. Quaternary ammonium germicides are not widely used in antibacterial personal care compositions, predominantly because of an inherent chemical incompatibility with the commonly used, and preferred, anionic surfactants, such as soaps, alcohol sulfates, alcohol ether sulfates, and the like.

Although a composition containing a quaternary ammonium compound and a selected anionic surfactant has been disclosed as being effective in some applications (e.g., U.S. Pat. No. 5,798,329), no reference disclosing such a combination for use in personal care compositions has been found. Accordingly, antibacterial personal care compositions based on quaternary ammonium germicides generally incorporate nonionic or amphoteric surfactants, and avoid anionic surfactants because of chemical incompatibility problems.

However, personal care compositions based on nonionic and/or amphoteric surfactants suffer in comparison to anionic surfactant-based compositions with respect to acceptable consumer properties, especially foam generation. It also is difficult to provide phase stable compositions having a consumer acceptable viscosity using a low to moderate level of nonionic and amphoteric surfactants.

In particular, when the nonionic/amphoteric surfactant level is low to moderate, the compositions initially are viscous, or thick, when first prepared, but often undergo phase separation under ambient, and especially under stressed (i.e., high temperature) storage conditions. Further, present-day antibacterial personal care compositions do not provide an effective antibacterial activity, especially against pathogenic Gram negative bacteria. Thus, a need exists for phase stable, efficacious antibacterial personal care compositions containing a quaternary ammonium germicide and a low or moderate level of nonionic or amphoteric surfactant, and that further are consumer acceptable and mild to the skin. A need also exists for phase stable compositions having a high viscosity and containing a phenolic antibacterial agent and an alkamine oxide surfactant.

An example of patents and published applications disclosing compositions comprising triclosan, surfactants, solvents, chelating agents, thickeners, buffering agents, and water is WO 98/01110. WO 98/01110 is directed to reducing skin irritation by employing a reduced amount of surfactant.

Fendler et al. U.S. Pat. No. 5,635,462 discloses compositions comprising PCMX and selected surfactants. The compositions disclosed therein are devoid of anionic surfactants and nonionic surfactants.

WO 97/46218 and WO 96/06152 disclose compositions based on triclosan, organic acids or salts, hydrotropes, and hydric solvents.

EP 0 505 935 discloses compositions containing PCMX in combination with nonionic and anionic surfactants, particularly nonionic block copolymer surfactants.

WO 95/32705 discloses a mild surfactant combination that can be combined with antibacterial compounds, like triclosan.

WO 95/09605 discloses antibacterial compositions containing anionic surfactants and alkylpolyglycoside surfactants.

WO 98/55096 discloses antimicrobial wipes having a porous sheet impregnated with an antibacterial composition containing an active antimicrobial agent, an anionic surfactant, an acid, and water, wherein the composition has a pH of about 3.0 to about 6.0.

Beerse et al. U.S. Pat. Nos. 5,968,539; 6,106,851; and 6,113,933 disclose antibacterial compositions having a pH of about 3 to about 6. The compositions contain an antibacterial agent, an anionic surfactant, and a proton donor.

N. A. Allawala et al., *J. Amer. Pharm. Assoc.—Sci. Ed.,* Vol. XLII, no. 5, pp. 267–275, (1953) discusses the antibacterial activity of active antibacterial agents in combination with surfactants.

A. G. Mitchell, *J. Pharm. Pharmacol.,* Vol. 16, pp. 533–537, (1964) discloses compositions containing PCMX and a nonionic surfactant that exhibit antibacterial activity. The compositions disclosed in the Mitchell publication exhibit antibacterial activity in at least 47 minutes contact time, thus the compositions are not highly effective.

Patents and published applications disclosing germicidal compositions containing a quaternary ammonium antibacterial agent include U.S. Pat. Nos. 5,798,329; 5,929,016; WO 97/15647; and EP 0 651 048, directed to antibacterial laundry detergents and antibacterial hard surface cleaners. Antibacterial compositions containing amphoteric surfactants are disclosed in U.S. Pat. Nos. 5,244,652; 5,389,676; 4,075,350; 4,062,976; 4,107,328; and 4,145,436.

Prior disclosures have not addressed the issue of providing an antibacterial composition that (a) affords an effective, fast, and broad spectrum control of bacteria at a neutral pH of about 5.5 to about 7.5, and especially at about 6.5 to about 7.3, (b) is phase stable, and (c) exhibits excellent esthetic properties, such as a high viscosity and a stable, copious foam generation.

An efficacious antibacterial composition having excellent esthetic properties has been difficult to achieve because of the chemical properties of the antibacterial agents and the surfactants, and the effects of a surfactant on an antibacterial agent. For example, nonionic and amphoteric surfactants do not provide a high foam level desired by consumers, and it is difficult to provide a phase stable, viscous composition. Anionic surfactants provide such properties, but cannot be formulated with quaternary ammonium antibacterial agents.

Accordingly, a need exists for an antibacterial composition that is highly efficacious against a broad spectrum of Gram positive and Gram negative bacteria in a short time period, and wherein the composition is viscous, phase stable, and provides consumer-acceptable esthetic properties, even in the absence of anionic surfactants. The present invention is directed to such antibacterial compositions.

SUMMARY OF THE INVENTION

The present invention relates to antibacterial compositions that provide a substantial reduction in Gram positive and Gram negative bacteria in less than about one minute. More particularly, the present invention relates to antimicrobial compositions containing a phenolic or quaternary ammonium antibacterial agent, an alkamine oxide surfactant, a cosurfactant, an optional—polymeric thickener, and water. The present antimicrobial compositions are free of anionic surfactants and zwitterionic surfactants, are phase stable, and possess excellent esthetic properties, such as foam height and stability.

Accordingly, one aspect of the present invention is to provide a stable, liquid antibacterial composition comprising: (a) about 0.05% to about 5%, by weight, of an antibacterial agent; (b) about 1% to about 15%, by weight, of an alkamine oxide surfactant; (c) about 1% to about 10%, by weight, of a nonionic cosurfactant, a cationic cosurfactant, or a mixture thereof; (d) 0% to about 5%, by weight, of a polymeric thickening agent, such as a hydrophobically modified alkoxylated compound; and (e) water. A present composition also is free of anionic and zwitterionic surfactants.

A present antibacterial composition is phase stable, has a pH of about 5.5 to about 7.5, and has a viscosity of about 0.1 to about 100 centipoise (cp) in the absence of a polymeric thickener, and up to about 10,000 cp when an optional thickening agent is present. The present compositions also exhibit excellent esthetic properties, such as foam character, which is unexpected for compositions free of anionic surfactants.

Yet another aspect of the present invention is to provide an antibacterial composition that exhibits a log reduction against Gram positive bacteria (i.e., *S. aureus*) of at least 2 after 30 seconds of contact.

Still another aspect of the present invention is to provide an antibacterial composition that exhibits a log reduction against Gram negative bacteria (i.e., *E. coli*) of at least 2.5 after 30 seconds of contact.

Another aspect of the present invention is to provide an antibacterial composition that exhibits a substantial log reduction against Gram positive and Gram negative bacteria, and has a pH of about 5.5 to about 7.5.

Another aspect of the present invention is to provide personal use products based on an antibacterial composition of the present invention, for example, a skin cleanser, a body splash, a surgical scrub, a wound care agent, a hand sanitizer gel, a disinfectant, a mouth wash, a pet shampoo, a hard surface sanitizer, and the like.

A further aspect of the present invention is to provide a method of reducing the Gram positive and/or Gram negative bacteria populations on animal tissue, including human tissue, by contacting the tissue, like the dermis, with a composition of the present invention for a sufficient time, such as about 15 seconds to 5 minutes, to reduce the bacteria level to a desired level.

The above and other novel aspects and advantages of the present invention are illustrated in the following, nonlimiting detailed description of the preferred embodiments.

DETAILED DESCRIPTION OF THE PREFERRED EMBODIMENTS

Personal care products incorporating an active antibacterial agent have been known for many years. Since the introduction of antibacterial personal care products, many claims have been made that such products provide antibacterial properties. However, to be most effective, an antibacterial composition should provide a high log reduction against a broad spectrum of organisms in as short a contact time as possible.

The antibacterial composition also should exhibit excellent esthetic properties in order to achieve consumer acceptance. The features of antibacterial efficacy and esthetic properties often are competing, wherein enhancing one feature is detrimental to the other. The present invention is directed to antibacterial compositions that unexpectedly exhibit both features.

As presently formulated, commercial liquid antibacterial soap compositions provide a poor to marginal time kill efficacy, i.e., rate of killing bacteria. Table 1 summarizes the kill efficacy of commercial products, each of which contains about 0.2% to 0.3%, by weight, triclosan (an antibacterial agent).

TABLE 1

Time Kill Efficacy of Commercial Liquid Hand Soaps

| Product | Organism (Log Reductions after 1 Minute Contact Time) | | |
| --- | --- | --- | --- |
| | Gram Positive S. aureus | Gram negative E. coil | Grain negative K. pneum. |
| Commercial Product A | 1.39 | 0.00 | 0.04 |
| Commercial Product B | 2.20 | 0.00 | 0.01 |
| Commercial Product C | 1.85 | 0.00 | 0.00 |

Present-day products especially lack efficacy against Gram negative bacteria, such as E. coli, which are of particular concern to human health. The present invention, therefore, is directed to antibacterial compositions having high broad spectrum antibacterial efficacy, as measured by a rapid kill of bacteria (i.e., time kill), which is to be distinguished from persistent kill. The present antibacterial compositions provide significantly improved time kill efficacy compared to prior compositions.

An important ingredient in antibacterial cleansing compositions is the surfactant, which acts as a solubilizer, cleanser, and foaming agent. Typically, the surfactant is an anionic surfactant, which provides excellent foam generation, good cleaning, and viscosity enhancement. However, the use of an anionic surfactant limits the range of useful antibacterial agents. For example, anionic surfactants and quaternary ammonium antibacterial agents are chemically incompatible. In addition, anionic surfactants tend to be harsh to the skin.

The substitution of a nonionic or amphoteric surfactant for an anionic surfactant in an antibacterial composition is not straightforward. For example, the substitution of a nonionic surfactant often leads to phase instability in a composition. In addition, nonionic and amphoteric surfactants do not generate the high foam levels that consumers equate to cleaning efficacy.

The present compositions are antibacterial compositions having an excellent effectiveness against both Gram negative and Gram positive bacteria, and that exhibit a rapid bacteria kill. The compositions also are phase stable, and exhibit excellent esthetic properties, such as viscosity and foam generation, even in the absence of anionic surfactants. As illustrated hereafter, an antibacterial composition of the present invention comprises: (a) about 0.05% to about 5%, by weight, of an antibacterial agent; (b) about 1% to about 15%, by weight, of an alkamine oxide surfactant; (c) about 1% to about 10%, by weight, of a nonionic cosurfactant, a cationic cosurfactant, or a mixture thereof; (d) 0% to about 5%, by weight, of a—polymeric thickener; and (e) water. The compositions also can further include additional optional ingredients disclosed hereafter, for example, a conditioning agent, a hydric solvent, a preservative, a hydrotrope, a pH adjuster, a dye, and a perfume. The compositions exhibit a log reduction against Gram positive bacteria of about 2 after 30 seconds contact. The compositions exhibit a log reduction against Gram negative bacteria of about 2.5 after 30 seconds contact.

The following illustrates nonlimiting embodiments of the present invention.

A. Antibacterial Agent

An antibacterial agent is present in a composition of the present invention in an amount of about 0.05% to about 5%, and preferably about 0.1% to about 3%, by weight of the composition. To achieve the full advantage of the present invention, the antibacterial agent is present in an amount of about 0.2% to about 2%, by weight, of the composition.

The antibacterial compositions can be ready to use compositions, which typically contain about 0.05% to about 2%, preferably about 0.1% to about 1.5%, and most preferably about 0.2% to about 1%, of an antibacterial agent, by weight of the composition. The antibacterial compositions also can be formulated as concentrates that are diluted before use with one to about 100 parts water to provide an end use composition. The concentrated compositions typically contain greater than about 0.1% and up to about 5%, by weight, of the antibacterial agent. Applications also are envisioned wherein the end use composition contains greater than 2%, by weight, of the antibacterial agent.

The amount of antibacterial agent in the composition is related to the end use of the composition, the identity and amount of alkamine oxide and cosurfactant in the composition, and the presence of optional ingredients in the composition. The amount of antibacterial agent is sufficient to achieve a bacteria kill in a short contact time, like 15 to 60 seconds.

The antimicrobial agents useful in the present invention are exemplified by the following classes of compounds used alone or in combination.

(1) Phenolic Antibacterial Agents (a) 2-Hydroxydiphenyl Compounds

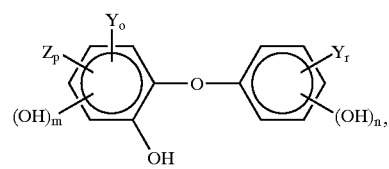

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1.

In preferred embodiments, Y is chlorine or bromine, m is 0, n is 0 or 1, o is 1 or 2, r is 1 or 2, and p is 0.

In especially preferred embodiments, Y is chlorine, m is 0, n is 0, o is 1, r is 2, and p is 0.

A particularly useful 2-hydroxydiphenyl compound has the structure:

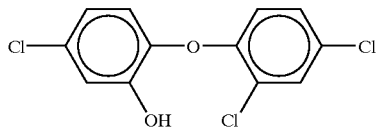

having the adopted name, triclosan, and available commercially under the tradename IRGASAN DP100, from Ciba Specialty Chemicals Corp., Greensboro, N.C. Another useful 2-hydroxydiphenyl compound is 2,2'-dihydroxy-5,5'-dibromodiphenyl ether. Additional bisphenolic compounds are disclosed in U.S. Pat. No. 6,113,933, incorporated herein by reference.

(b) Phenol Derivatives

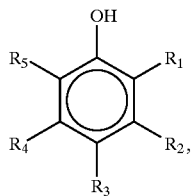

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl; and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in WO 98/55096 and U.S. Pat. No. 6,113,933, incorporated herein by reference.

(c) Diphenyl Compounds

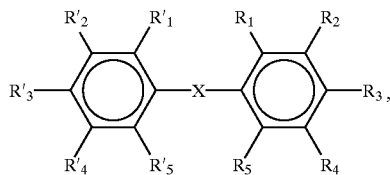

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3', 5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine. Other diphenyl compounds are listed in WO 98/55096, incorporated herein by reference.

(2) Quaternary Ammonium Antibacterial Agents

Useful quaternary ammonium antibacterial agents have a general structural formula:

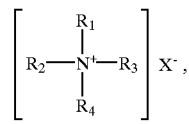

wherein at least one of $R_1$, $R_2$, $R_3$, and $R_4$ is an alkyl, aryl, or alkaryl substituent containing 6 to 26 carbon atoms. Alternatively, any two of the R substituents can be taken together, with the nitrogen atom, to form a five- or six-membered aliphatic or aromatic ring. Preferably, the entire ammonium cation portion of the antibacterial agent has a molecular weight of at least 165.

The substituents $R_1$, $R_2$, $R_3$, and $R_4$ can be straight chained or can be branched, but preferably are straight chained, and can include one or more amide, ether, or ester linkage. In particular, at least one substituent is $C_6$–$C_{26}$alkyl, $C_6$–$C_{26}$alkoxyaryl, $C_6$–$C_{26}$alkaryl, halogen-substituted $C_6$–$C_{26}$alkaryl, $C_6$–$C_{26}$alkylphenoxyalkyl, and the like. The remaining substituents on the quaternary nitrogen atom other than the above-mentioned substituent typically contain no more than 12 carbon atoms. In addition, the nitrogen atom of the quaternary ammonium antibacterial agent can be present in a ring system, either aliphatic, e.g., piperdinyl, or aromatic, e.g., pyridinyl. The anion X can be any salt-forming anion which renders the quaternary ammonium compound water soluble. Anions include, but are not limited to, a halide, for example, chloride, bromide, or iodide, methosulfate, and ethosulfate.

Preferred quaternary ammonium antibacterial agents have a structural formula:

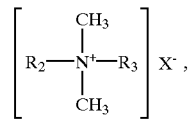

wherein $R_2$ and $R_3$, independently, are $C_8$–$C_{12}$alkyl, or $R_2$ is $C_{12}$–$C_{16}$alkyl, $C_8$–$C_{18}$alkylethoxy, or $C_8$–$C_{18}$alkylphenylethoxy, and $R_3$ is benzyl, and X is halo, methosulfate, ethosulfate, or p-toluenesulfonate. The alkyl groups $R_2$ and $R_3$ can be straight chained or branched, and preferably are linear.

The quaternary ammonium antibacterial agent in a present composition can be a single quaternary ammonium compound, or a mixture of two or more quaternary ammonium compounds. Particularly useful quaternary ammonium antibacterial agents include dialkyl($C_8$–$C_{10}$) dimethyl ammonium chlorides (e.g., dioctyl dimethyl ammonium chloride), alkyl dimethyl benzyl ammonium chlorides (e.g., benzalkonium chloride and myristyl dimethylbenzyl ammonium chloride), alkyl methyl dodecyl benzyl ammonium chloride, methyl dodecyl xylene-bis-trimethyl ammonium chloride, benzethonium chloride, dialkyl methyl benzyl ammonium chloride, alkyl dimethyl ethyl ammonium bromide, and an alkyl tertiary amine. Polymeric quaternary ammonium compounds based on these monomeric structures also can be used in the present invention. One example of a polymeric quaternary ammonium compound is POLYQUAT®, e.g., a 2-butenyl dimethyl ammonium chloride polymer. The above quaternary ammonium compounds are available commercially under the tradenames BARDAC®, BTC®, HYAMINE®, BARQUAT®, and LONZABAC®, from suppliers such as Lonza, Inc., Fairlawn, N.J. and Stepan Co., Northfield, Ill.

Additional examples of quaternary ammonium antibacterial agents include, but are not limited to, alkyl ammonium halides, such as cetyl trimethyl ammonium bromide; alkyl aryl ammonium halides, such as octadecyl dimethyl benzyl ammonium bromide; N-alkyl pyridinium halides, such as N-cetyl pyridinium bromide; and the like. Other suitable quaternary ammonium antibacterial agents have amide, ether, or ester moieties, such as octylphenoxyethoxy ethyl dimethyl benzyl ammonium chloride, N-(laurylcocoaminoformylmethyl)pyridinium chloride, and the like. Other classes of quaternary ammonium antibacterial agents include those containing a substituted aromatic nucleus, for example, lauryloxyphenyl trimethyl ammonium chloride, cetylaminophenyl trimethyl ammonium methosulfate, dodecylphenyl trimethyl ammonium methosulfate, dodecylbenzyl trimethyl ammonium chloride, chlorinated dodecylbenzyl trimethyl ammonium chloride, and the like.

Specific quaternary ammonium antibacterial agents include, but are not limited to, behenalkonium chloride, cetalkonium chloride, cetarylalkonium bromide, cetrimonium tosylate, cetyl pyridinium chloride, lauralkonium bromide, lauralkonium chloride, lapyrium chloride, lauryl pyridinium chloride, myristalkonium chloride, olealkonium chloride, and isostearyl ethyldimonium chloride. Preferred quaternary ammonium antibacterial agents include benzalkonium chloride, benzethonium chloride, cetyl pyridinium bromide, and methylbenzethonium chloride.

B. Alkamine Oxide Surfactant

In addition to an antibacterial agent, a present antimicrobial composition also contains an alkamine oxide surfactant. The alkamine oxide surfactant is present in an amount of about 1% to about 15%, and preferably about 1.5% to about 10%, by weight, of the composition. To achieve the full advantage of the present invention, a present antibacterial composition contains about 2% to about 8%, by weight, of the alkamine oxide surfactant.

Ready-to-use compositions typically contain about 1% to about 10%, preferably about 1% to about 5%, and most preferably, 1% to about 3%, of alkamine oxide surfactant, by weight, of the composition. Concentrated compositions suitable for dilution typically contain greater than about 5%, by weight, of an alkamine oxide surfactant.

The amount of alkamine oxide surfactant present in the composition is related to the amount and identity of the antibacterial agent in the composition, to the identity of the alkamine oxide surfactant, and the end use of the composition.

An alkamine oxide useful in the present invention contains at least one long hydrocarbon chain containing at least eight carbon atoms. One class of amine oxides is the alkyl di(lower alkyl) amine oxides, wherein the alkyl group contains 8 to 22, and preferably about 10 to about 16, carbon atoms, and can be straight or branched chain, saturated or unsaturated. The lower alkyl groups contain 1 to 7 carbon atoms, and typically are methyl. Specific examples include, but are not limited to, lauryl dimethyl amine oxide, myristyl dimethyl amine oxide, dimethyl cocoamine oxide, dimethyl (hydrogenated tallow)amine oxide, myristyl/palmityl dimethyl amine oxide, myristyl/lauryl dimethyl amine oxide, cetyl dimethyl amine oxide, stearyl dimethyl amine oxide, and myristyl/cetyl dimethyl amine oxide. These alkamine oxides have a general structural formula

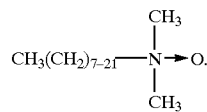

Another class of useful amine oxides includes alkyl di(hydroxy lower alkyl)amine oxides in which the alkyl group contains 8 to 22, and preferably about 10 to about 16 carbon atoms, and can be straight or branched chain, saturated or unsaturated. Specific examples, include, but are not limited to, bis(2-hydroxyethyl)cocoamine oxide, bis(2-hydroxyethyl)tallow amine oxide, and bis(2-hydroxyethyl)stearylamine oxide. These alkamine oxides have a general structural formula

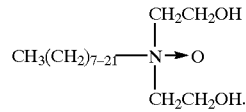

Additional useful amine oxides are termed alkamidopropyl di(lower alkyl)amine oxides in which the alkyl group contains 8 to 22, and preferably about 10 to about 16 carbon atoms, and can be straight or branched chain, saturated or unsaturated. Examples are cocoamidopropyl dimethyl amine oxide and tallowamidopropyl dimethyl amine oxide. These alkamine oxides have a general structural formula

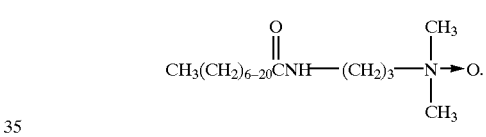

Further useful amine oxides are termed alkylmorpholine oxides in which the alkyl group contains 8 to 22, and preferably about 10 to about 16, carbon atoms, and can be straight or branched chain, saturated or unsaturated. Alkamine oxides are commercially available, for example, from Stepan Co., Northfield, Ill., and Lonza Inc., Fairlawn, N.J.

The above classes of alkamine oxide surfactants contain a $C_8$–$C_{22}$ alkyl group selected from, for example, octyl, decyl, undecyl, lauryl, tridecyl, myristyl, cetyl, stearyl, isostearyl, oleyl, and mixtures thereof. Examples of amine oxide surfactants include, but are not limited to, decyl dimethylamine oxide, lauryl dimethylamine oxide, stearyl dimethylamine oxide, oleyl dimethylamine oxide, coco dihydroxyethylamine oxide, cetyl N,N-dihydroxyethylamine oxide, oleyl N,N-dihydroxyethylamine oxide, cocamine oxide, cocamidopropylamine oxide, lauramidopropylamine oxide, oleamine oxide, oleamidopropylamine oxide, wheat germamidopropylamine oxide, isostearamido-propylamine oxide, stearamine oxide, stearamido-propylamine oxide, cocomorpholine oxide, decylamine oxide, dihydroxyethyl $C_8$–$C_{10}$ alkoxypropylamine oxide, dihydroxyethyl $C_9$–$C_{11}$ alkoxypropylamine oxide, dihydroxyethyl $C_{12}$–$C_{11}$ alkoxypropylamine oxide, dihydroxyethyl cocamine oxide; dihydroxyethyl stearamine oxide, dihydroxyethyl tallowamine oxide, hydrogenated tallow amine oxide, hydroxyethyl hydroxypropyl$C_{12}$–$C_{15}$ alkoxypropylamine oxide, isostearamidopropyl morpholine oxide, myristamidopropylamine oxide, myristamine oxide, palmitamidopropylamine oxide, palmitamine oxide, PEG-3 lauramine oxide, tallow amidopropylamine oxide, tallow amine oxide, undecylenamidopropylamine oxide, and mixtures thereof. Preferred alkamine oxide surfactants are the alkyl di(lower alkyl)amine oxides in which the alkyl group contains about 12 to about 16 carbon atoms, including lauramine oxide, myristamine oxide, cocamine oxide, cetamine oxide, and mixtures thereof. Most preferably, the alkamine oxide surfactant comprises lauramine oxide.

In some preferred embodiments, an antibacterial composition of the present invention contains a blend of alkamine oxide surfactants. In most preferred embodiments, a first component of the alkamine oxide blend contains twelve or fewer carbon atoms and a second component contains more than twelve carbon atoms.

C. Cosurfactant

In addition to the antibacterial agent and alkamine oxide, the antibacterial composition contains about 1% to about 10%, and preferably about 1.5% to about 8%, by weight, of a nonionic and/or cationic cosurfactant. To achieve the full advantage of the present invention, the composition contains about 2% to about 6%, by weight of the composition, of a cosurfactant.

The cosurfactant can be (a) a nonionic surfactant, such as a polyoxyethylene alcohol condensate, an alkylpolyglucoside (APG) surfactant, and the like, (b) a cationic surfactant, such as an amine salt, a quaternary ammonium surfactant, an amidopropyl betaine monoethanolamide, and the like, or (c) a mixture thereof. Examples of cosurfactants include, but are not limited to, lauryl polyglucose, decyl polyglucose (e.g., PLANTAREN 2000N from Cognis Care Chemicals, Ambler, Pa.), cocamidopropylbetaine MEA chloride (MONTALAINE C40 from Seppic, Paris, France), and sunflower seed amidopropylethyldimonium ethosulfate (MACKERNIUM DY83, McIntyre Chemical Co., University Park, Ill.). If the cosurfactant is a quaternary ammonium surfactant, such a surfactant does not exhibit the typical antibacterial properties of a quaternary ammonium antibacterial agent.

Typically, a nonionic cosurfactant has a hydrophobic base, such as a long chain alkyl group or an alkylated aryl group, and a hydrophilic chain comprising a ethoxy and/or propoxy moieties. The hydrophilic chain preferably contains ethoxy moieties. As defined herein, a "nonionic cosurfactant" has a hydrophobic base having an alkyl group containing six to eighteen carbon atoms, and an average of one to about twenty ethoxy and/or propoxy moieites. Examples of classes of nonionic cosurfactants include ethoxylated alkylphenols, ethoxylated and propoxylated fatty alcohols, alkylpolyglucosides, polyethylene glycol ethers of sorbitol, ethylene oxide-propylene oxide block copolymers, ethoxylated esters of fatty ($C_8$–$C_{14}$) acids, condensation products of ethylene oxide with long chain amines or amides, and mixtures thereof.

Examples of nonionic cosurfactants include, but are not limited to, $C_{11}$–$C_{15}$pareth-20, ceteth-12, dodoxynol-12, laureth-15, polysorbate 20, an ethoxylated nonylphenol, ethoxylated octylphenol, ethoxylated dodecylphenol, or ethoxylated fatty ($C_6$–$C_{18}$) alcohol, including 4 to 20 ethylene oxide moieties, glycereth-12, trideceth-9, trideceth-10, trideceth-11, trideceth-12, trideceth-15, sorbeth-20, dodoxynol-9, dodoxynol-12, chlorodeceth-14, chloeth-10, dihydrocholeth-15, isoceteth-10, isoceteth-20, isolaureth-10, isosteareth-10, isosteareth-12, isosteareth-20, laneth-10, laneth-15, laneth-16, laneth-20, oleth-9, oleth-10, oleth-12, oleth-15, oleth-16, oleth-20, steareth-10, steareth-11, steareth-13, steareth-15, steareth-16, steareth-20, talloweth-6, laureth-9, laureth-10, laureth-11, laureth-12, laureth-13, laureth-14, laureth-15, laureth-20, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1–246 and 266–273; in the *CTFA International Cosmetic Ingredient Dictionary, Fourth Ed.*, Cosmetic, Toiletry and Fragrance Association, Washington, D.C. (1991) (hereinafter the *CTFA Dictionary*) at pages 1–651; and in the *CTFA Cosmetic Ingredient Handbook, First Ed.*, Cosmetic, Toiletry and Fragrance Association, Washington, D.C. (1988) (hereafter the *CTFA Handbook*), at pages 86–94, each incorporated herein by reference.

Cationic cosurfactants include a quaternary surfactant having a structural formula

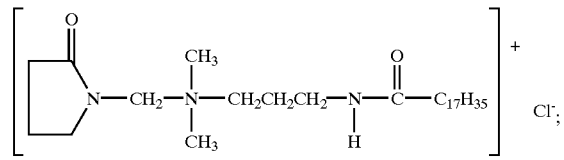

a quaternized phosphate ester, such as PHOSPHOLIPID SV, available from Mona Industries, Paterson, N.J., e.g., stearamidopropyl phosphatidyl PG-dimonium chloride, linoleamidopropyl phosphatidyl PG-dimonium chloride, coco phosphatidyl PG-dimonium chloride, cocamidopropyl phosphatidyl PG-dimonium chloride, borageamidopropyl phosphatidyl PG-dimonium chloride, and cocohydroxyethyl phosphatidyl PG-imidazolinium chloride; and other quaternized phosphate esters disclosed in Mayhew et al. U.S. Pat. No. 4,209,449. Additional quaternary ammonium surfactants can be found in the *CTFA Handbook* at pages 40–42, incorporated herein by reference.

In accordance with an important feature of the present invention, a present antibacterial composition is free of anionic surfactants and zwitterionic surfactants. The phrase "free" of an anionic and zwitteronic surfactant is defined as meaning that the composition contains 0% to about 0.25% by weight, in total, of an anionic surfactant and/or zwitterionic surfactant. In particular, an anionic surfactant and/or zwitterionic surfactant may be present in an antibacterial composition in a total amount of 0.25% or less either as a by-product or as a component of an ingredient in the composition, but an anionic or zwitterionic surfactant is not intentionally introduced into the composition. For example, the present compositions are free of sarcosinates, taurates, amide sulfosuccinates, alkoamphoglycinates, alkoamphopropionates, alkoamphocarboxyglycinates, alkoamphocarboxypropionates, alkoamphopropylsulonates, alkamidopropyl betaines, alkamidopropyl hydroxysultaines, alkylaminopropionates, alkyliminopropionates, phosphobetaines, phosphitaines, alkyl sulfates, alkyl sulfonates, salts of fatty acids, alpha-olefin sulfonates, alkyl ether sulfates, and alkyl carbonates.

Preferred compositions of the present invention contain decyl polyglucose, sunflower seed amidopropylethyldimonium ethosulfate, or a mixture thereof as the cosurfactant.

D. Optional Polymeric Thickener

In addition to the antibacterial agent, alkamine oxide surfactant, and cosurfactant, an antibacterial composition of the present invention optionally can contain a thickener. The thickener is present in an amount of 0% to about 5%, and preferably 0.25% to about 4%, by weight, of the composition. To achieve the full advantage of the present invention, the thickener is present in an amount of about 0.5% to about 3%, by weight, of the composition.

A polymeric thickener typically is present in a sufficient amount to provide a composition having a viscosity of about 100 to about 10,000 centipoise, preferably about 300 to about 6000 centipoise, and more preferably about 500 to about 5000 centipoise. To achieve the full advantage of the present invention, an antimicrobial composition has a viscosity of about 2000 to about 5000 centipoise. In the absence of a polymeric thickener, a present composition has a viscosity of about 0.1 to about 100 centipoise.

For some applications, a polymeric thickener is an important ingredient of the present invention because compositions containing an alkamine oxide often have a low viscosity, i.e., appear "watery," and hence have a reduced consumer appeal. The addition of a thickener to the composition is not straightforward, however, because the thickener must perform multiple functions, such as increasing the viscosity of the composition, without adversely affecting the phase stability of the composition and without reducing the typical low foam height generated by an alkamine oxide. Surprisingly, various polymeric thickeners successfully increase the viscosity of a present antibacterial composition, while maintaining excellent phase stability and providing excellent foam properties.

A polymeric thickener of the present invention can be (a) a cellulose thickener, (b) a hydrophobically modified polyethylene glycol (PEG) or hydrophobically modified polypropylene glycol (PPG), or (c) a hydrophobic alkoxylated alcohol. A cellulose thickener can be a nonionic cellulose or a cationic cellulose. Useful cellulose thickeners include, but are not limited to, hydroxyethylcellulose, hydroxybutyl methylcellulose, hydroxypropyl methylcellulose, hydroxypropylcellulose, polyquaternium 10, polyquaternium 4, hydroxypropyl methylcellulose, and hydroxyethyl ethylcellulose.

A hydrophobic PEG, PPG, or alkoxylated alcohol contains a hydrophobic hydrocarbon moiety, either alkyl or alkylated aryl. The alkyl group of the hydrophobic moiety contains fourteen carbon atoms, or more (e.g., up to thirty carbon atoms). Such thickeners further contain an average of at least twenty ethoxy and/or propoxy moieties.

Examples of a hydrophobically modified PEG or hydrophobically modified PPG include, for example, PEG-20 through PEG-200, or PPG-20 through PPG-34, either having a hydrophobic moiety attached thereto or copolymerized with a hydrophobic monomer. The hydrophobic monomer can be a $C_{14}$–$C_{18}$ glycol, for example. The hydrophobic moiety can be an alkylated phenol residue, such as a nonylphenol residue, a fatty acid residue, a fatty amide residue, a fatty amine residue, and similar residues having a long-chain alkyl (e.g., $C_{14}$–$C_{22}$) and/or an aryl component. Examples of an alkoxylated alcohol include a $C_{14}$–$C_{20}$ alcohol alkoxylate with 20 to 100 moles of ethylene oxide and/or propylene oxide, and having a hydrophobic moiety present in the molecule.

Specific examples of hydrophobically modified polymeric thickeners include, but are not limited to, PEG-120 methyl glucose dioleate, PPG-14 palmeth-60 alkyl, ceteareth-60 myristyl glycol, methoxy PEG-22/dodecyl glycol copolymer, methyl gluceth-20, PEG-20 castor oil, PEG-25 castor oil, PEG-30 castor oil, PEG-36 castor oil, PEG-40 castor oil, PEG-50 castor oil, PEG-60 castor oil, PEG-100 castor oil, PEG-45/dodecyl glycol copolymer, PEG-20 hydrogenated castor oil, PEG-25 hydrogenated castor oil, PEG-30 hydrogenated castor oil, PEG-40 hydrogenated castor oil, PEG-50 hydrogenated castor oil, PEG-60 hydrogenated castor oil, PEG-80 hydrogenated castor oil, PEG-100 hydrogenated castor oil, PPG-20 lanolin alcohol PPG-30 lanolin alcohol ether, PPG-25-laureth-25, PPG-20 oleyl ether, PPG-23 oleyl ether, PPG-30 oleyl ether, PPG-37 oleyl ether, PPG-50 oleyl ether, PPG-20 methyl glucose ether, PPG-20 methyl glucose ether acetate, PEG-20 lanolin, PEG-24 lanolin, PEG-27 lanolin, PEG-30 lanolin, PEG-40 lanolin, PEG-50 lanolin, PEG-60 lanolin, PEG-75 lanolin, PEG-85 lanolin, PEG-10 lanolin, PEG-75 lanolin oil, PEG-75 lanolin wax, PEG-20 methyl glucose sesquistereate, PEG-20-PPG-10 glyceryl stearate, PEG-25 propylene glycol stearate, PEG-75 propylene glycol stearate, PEG-120 propylene glycol stearate, PEG-25 soya sterol, PEG-40 soya sterol, talloweth-60 myristyl glycol, and mixtures thereof.

E. Optional Ingredients

An antibacterial composition of the present invention also can contain optional ingredients known to persons skilled in the art. For example, the composition can contain a hydric solvent and/or a hydrotrope. The present compositions also can contain other optional ingredients, such as skin conditioners, dyes, and fragrances, that are present in a sufficient amount to perform their intended function and do not adversely affect the antibacterial efficacy or consumer acceptance of the composition. Such optional ingredients typically are present, individually, from 0% to about 5%, by weight, of the composition, and, collectively, from 0% to about 20%, by weight, of the composition.

Classes of optional ingredients include, but are not limited to, dyes, fragrances, pH adjusters, skin conditioners and emollients, buffering agents, foam stabilizers, antioxidants, preservatives, foam enhancers, hydrotropes, water softening agents, chelating agents, opacifiers, and similar classes of optional ingredients known to persons skilled in the art.

Specific optional ingredients include alkanolamides as foam boosters and stabilizers; inorganic phosphates, sulfates, and carbonates as buffering agents; mono-, di-, and triglycerides (e.g., glycerol monolaurate) as opacifiers, viscosity modifiers, or skin conditioners; EDTA and phosphates as chelating agents; and acids and bases as pH adjusters.

Examples of preferred basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art, alone or in combination, can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

With respect to pH adjusters, a present composition has a pH of about 5.5 to about 7.5 to provide a high, broad-spectrum antibacterial efficacy. An optional pH adjuster can be used in a sufficient amount to provide a pH of about 5.5 to about 7.5, or a preferred pH of about 6 to about 7.3.

An alkanolamide used to provide foam enhancement and foam stability can be, but is not limited to, cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof.

Optional skin conditioners and emollients include, but are not limited to, an ester having at least 10 carbon atoms, and preferably 10 to about 32 carbon atoms. Suitable esters include those comprising an aliphatic alcohol having about 8 to about 20 carbon atoms and an aliphatic or aromatic carboxylic acid including 2 to about 12 carbon atoms, or conversely, an aliphatic alcohol having 2 to about 12 carbon atoms with an aliphatic or aromatic carboxylic acid including 8 to about 20 carbon atoms. The ester is either straight chained or branched. Preferably, the ester has a molecular weight of less than about 500 and provides emollient properties. Suitable esters, therefore, include, for example, but are not limited to:

(a) aliphatic monohydric alcohol esters, including, but not limited to, myristyl propionate, isopropyl isostearate, isopropyl myristate, isopropyl palmitate, cetyl acetate, cetyl propionate, cetyl stearate, isodecyl neopentanoate, cetyl octanoate, and isocetyl stearate;

(b) aliphatic di- and triesters of polycarboxylic acids, including, but not limited to, diisopropyl adipate, diisostearyl fumarate, dioctyl adipate, and triisostearyl citrate;

(c) aliphatic polyhydric alcohol esters, including, but not limited to, propylene glycol dipelargonate;

(d) aliphatic esters of aromatic acids, including, but not limited to, $C_{12}$–$C_{15}$ alcohol esters of benzoic acid, octyl salicylate, sucrose benzoate, and dioctyl phthalate.

Numerous other esters are listed in the CTFA Handbook at pages 24 through 26, incorporated herein by reference.

A present antibacterial composition also optionally can include an oil. Examples of oils that can be included in the composition include, but are not limited to, apricot kernel oil, avocado oil, $C_{30}$–$C_{46}$ piscine oil, castor oil, chaulmoogra oil, cherry pit oil, coconut oil, corn oil, cottonseed oil, egg oil, ethiodized oil, grape seed oil, hazel nut oil, hybrid safflower oil, lanolin oil, linseed oil, menhaden oil, mink oil, moringa oil, neatsfoot oil, olive husk oil, olive oil, palm kernel oil, palm oil, peach kernel oil, peanut oil, pengawar djambi oil, rapeseed oil, rice bran oil, safflower oil, sesame oil, soybean oil, sunflower seed oil, sweet almond oil, walnut oil, wheat germ oil, cod liver oil, hydrogenated castor oil, hydrogenated coconut oil, hydrogenated cottonseed oil, hydrogenated jojoba oil, hydrogenated menhaden oil, hydrogenated palm kernel oil, white petrolatum, hydrogenated palm oil, hydrogenated peanut oil, hydrogenated shark liver oil, hydrogenated soybean oil, hydrogenated vegetable oil, jojoba oil, shark liver oil, synthetic jojoba oil, tall oil, vegetable oil, bay oil, cottonseed oil, and mixtures thereof.

A composition of the present invention also optionally can contain 0% to about 20%, by weight, of a hydric solvent, and 0% to about 20%, by weight, of a hydrotrope.

As used herein, the term "hydric solvent" is defined as a water-soluble organic compound containing one to six, and typically one to three, hydroxyl groups. The term "hydric solvent" therefore encompasses water-soluble alcohols, diols, triols, and polyols. Specific examples of hydric solvents include, but are not limited to, methanol, ethanol, isopropyl alcohol, n-butanol, n-propyl alcohol, ethylene glycol, propylene glycol, glycerol, diethylene glycol, dipropylene glycol, tripropylene glycol, hexylene glycol, butylene glycol, 1,2,6-hexanetriol, sorbitol, PEG-4, and similar hydroxyl-containing compounds.

A hydrotrope is a compound that has the ability to enhance the water solubility of other compounds. An optional hydrotrope utilized in the present invention typically is a short-chain alkyl aryl sulfonate. Specific examples of hydrotropes include, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, and disodium succinate.

A present antibacterial composition also can contain a preservative in an amount of 0% to about 0.5% by weight. Examples of preservatives include, but are not limited to, sorbic acid, potassium sorbate, the parabens (like benzylparaben), imidazolinylurea, methylchloroisothiazolinone, and the hydantoins, like DMDM hydantoin. Additional preservatives as disclosed in the CTFA Handbook at page 78, incorporated herein by reference.

A present antibacterial composition further can contain an antioxidant and/or an ultraviolet light (UV) absorber, each independently in an amount of 0% to about 0.5% by weight. Examples of antioxidants and UV absorbers include, but are not limited to, BHA, BHT, sodium ascorbate, potassium sulfite, erythorbic acid, benzophenone-1 through benzophenone-12, and PABA. Additional antioxidants and UV absorbers can be found in the CTFA Handbook at pages 78 and 98, incorporated herein by reference.

F. Carrier

The carrier of a present antibacterial composition comprises water.

An antibacterial composition of the present invention does not rely upon a low pH or a high pH to provide a rapid reduction in bacterial populations. Antibacterial compositions of the present invention have a pH of about 5.5 to about 7.5, and preferably about 6 to about 7.3. Within this pH range, the present compositions effectively reduce Gram positive and Gram negative bacterial populations, and are consumer acceptable, i.e., have a consumer acceptable viscosity, are mild to the skin, are phase stable, and generate a high, stable foam. Such results are surprising for an antibacterial composition that is free of an anionic surfactant.

To demonstrate the new and unexpected results provided by the antibacterial compositions of the present invention, the following Examples were prepared, and the ability of the compositions to control Gram positive and Gram negative bacteria was determined. The weight percentage listed in each of the following examples represents the actual, or active, weight amount of each ingredient present in the composition. The compositions were prepared by blending the ingredients, as understood by those skilled in the art and as described below.

The following materials were used as ingredients in the examples. The source of each ingredient, and its abbreviation, are summarized below:

| Chemical Name | Tradename | Active % | Supplier |
|---|---|---|---|
| (a) Benzethonium chloride (BZC) | same | 100 | Lonza |
| (b) Decyl polyglucose | PLANTAREN 2000N | 50 | Cognis |
| (c) Glycerin | same | 100 | Dial |
| (d) Lauramine oxide | MACKAMINE LO | 30 | McIntyre |
| (e) Sunflower seed amidopropyl ethyldimonium ethylsulfate | MACKERNIUM SFES | 80 | McIntyre |
| (f) Orchophenylphenol | DOWICIDE 1 | 100 | Dow |
| (g) Triclosan (TCS) | IRGASAN DP300 | 100 | Ciba |

-continued

| Chemical Name | Tradename | Active % | Supplier |
|---|---|---|---|
| (h) PEG-120 methyl glucose dioleate | GLUCAMATE DOE120 | 100 | Amerchol |
| (i) Hydroxyethyl ethylcellulose | ELFACOS CD481 | 100 | Akzo Nobel |
| (j) Ceteareth-60 myristyl glycol | ELFACOS GT282S | 100 | Akzo Nobel |
| (k) PPG-14 palmeth-60 Alkyl | ELFACOS T212 | 100 | Akzo Nobel |
| (l) Hydroxypropyl methylcellulose | METHOCEL 40-101 | 100 | Dow |
| (m) Polyquaternium 10 | CELQUAT SC-230M | 100 | National Starch |
| (n) Cocamidopropyl betaine MEA chloride | MONTALAINE C-40 | 40 | Seppic |
| (o) Stearyldimethyl-ethylhexyl ammonium methosulfate | ARQUAD HTL8-MS | 80 | Akzo Nobel |
| (p) Water-unless otherwise indicated, the water was prepared as follows: deionized (DI) water was distilled once through a Corning AG-3 water still | | | |

The following methods were used in the preparation and testing of the examples:

a) Determination of Rapid Germicidal (Time Kill) Activity of Antibacterial Products. The activity of antibacterial compositions was measured by the time kill method, whereby the survival of challenged organisms exposed to an antibacterial test composition is determined as a function of time. In this test, a diluted aliquot of the composition is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated. In general, the time kill method is known to those skilled in the art.

The composition can be tested at any concentration from 0–100%. The choice of which concentration to use is at the discretion of the investigator, and suitable concentrations are readily determined by those skilled in the art. For example, viscous samples usually are tested at 50% dilution, whereas nonviscous samples are not diluted. The test sample is placed in a sterile 250 ml beaker equipped with a magnetic stirring bar and the sample volume is brought to 100 ml, if needed, with sterile deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about $10^8$ colony forming units per ml (cfu/ml).

The table below lists-the test bacterial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| Staphylococcus aureus | 6538 | S. aureus |
| Escherichia coli | 11229 | E. coil |
| Klebsiella pneumoniae | 10031 | K. pneum. |

S. aureus is a Gram positive bacteria, whereas E. coli and K. pneum. are Gram negative bacteria.

The beaker containing the test composition is placed in a water bath (if constant temperature is desired), or placed on a magnetic stirrer (if ambient laboratory temperature is desired). The sample then is inoculated with 1.0 ml of the test bacteria suspension. The inoculum is stirred with the test composition for the predetermined contact time. When the contact time expires, 1.0 ml of the test composition/bacteria mixture is transferred into 9.0 ml of Tryptone-Histidine-Tween Neutralizer Solution (THT). Decimal dilutions to a countable range then are made. The dilutions can differ for different organisms. Plate selected dilutions in triplicate on TSA+ plates (TSA+ is Trypticase Soy Agar with Lecithin and Polysorbate 80). The plates then are incubated for 25±2 hours, and the colonies are counted for the number of survivors and the calculation of percent or log reduction. The control count (numbers control) is determined by conducting the procedure as described above with the exception that THT is used in place of the test composition. The plate counts are converted to cfu/ml for the numbers control and samples, respectively, by standard microbiological methods.

The log reduction is calculated using the formula

Log reduction=$log_{10}$ (numbers control)–$log_{10}$ (test sample survivors).

The following table correlates percent reduction in bacteria population to log reduction:

| % Reduction | Log Reduction |
|---|---|
| 90 | 1 |
| 99 | 2 |
| 99.9 | 3 |
| 99.99 | 4 |
| 99.999 | 5 |

EXAMPLE 1

This example shows that compositions thickened with an optional hydrophobically modified polymeric thickener (i.e., ELFACOS CD 481) are phase stable.

| | Wt. Percent | | | | |
|---|---|---|---|---|---|
| Ingredient | A | B | C | D | E |
| BZC | 0.25 | 0.25 | 0.25 | 0.25 | 0.25 |
| ELFACOS CD 481 (polymeric thickener) | 1.0 | 1.0 | 1.0 | 1.0 | 1.0 |
| PLANTAREN 2000 N | — | 1.44 | — | 3.25 | — |
| Glycerin | 2.5 | 2.5 | 2.5 | 2.5 | 2.5 |
| MACKAMINE LO | 6.0 | 2.25 | 4.5 | 5.04 | 4.5 |

-continued

| Ingredient | Wt. Percent | | | | |
|---|---|---|---|---|---|
| | A | B | C | D | E |
| Citric acid (25%) | 1.75 | 0.75 | 1.75 | 2.0 | 1.65 |
| MACKERNIUM SFES (cosurfactant) | — | — | — | — | 3.2 |
| Water | q.s. | q.s. | q.s. | q.s. | q.s. |

All Samples 1A-1E exhibited a consumer acceptable viscosity and were physically stable with no indications of phase separation, even when stored under accelerated aging conditions (10 days at 60° C.)

EXAMPLE 2

This example shows a surprising increase in viscosity in compositions containing an optional polymeric thickener and a viscosity-enhancing additive (i.e., sodium chloride). A different polymeric thickener (i.e., GLUCAMATE DOE120) was used than in Example 1.

| Ingredient | Wt. % | |
|---|---|---|
| | A | B |
| BZC | 0.25 | 0.25 |
| MACKAMINE LO | 4.5 | 4.5 |
| Glycerin | 2.5 | 2.5 |
| MACKERNIUM SFES | 3.2 | 3.2 |
| GLUCAMATE DOE120 (polymeric thickener) | 3.0 | 3.0 |
| Sodium chloride (NaCl) (viscosity enhancer) | 0.1 | 0.1 |
| Citric Acid (25%) | 1.5 | 1.5 |
| DOWICIDE 1[1] (antibacterial agent) | — | 0.25 |
| Water | q.s. | q.s. |

[1] orthophenylphenol

The viscosity of Sample 2A was 511 cp, and the viscosity of Sample 2B was 2770 cp. An unexpected increase in viscosity was observed upon addition of 0.25% DOWICIDE 1 to the composition (Sample 2B).

All viscosity measurements herein were obtained using a Brookfield Viscometer, Model DV II (digital), LVT, Speed 12, Spindle Number #3. When determining viscosity, a 200 ml sample is poured into a 250 ml beaker and allowed to equilibrate temperature to 25° C.+/−0.5° C. The Brookfield Viscometer is standardized according to the manufacturer's directions. The sample is placed under the spindle and is raised until the surface of the liquid is at the "notch," ensuring that no air bubbles are trapped underneath the spindle. The viscometer is engaged and the reading for viscosity is taken after one minute. If the reading is unstable, readings are taken at 30–45 seconds, and again at 75 seconds, and the range of readings is reported.

EXAMPLE 3

This example shows that triclosan can be substituted for benzethonium chloride as the antibacterial agent in a composition of the present invention.

| Ingredient | Wt. % | |
|---|---|---|
| | A | B |
| BZC | 0.25 | — |
| TCS (antibacterial agent) | — | 0.25 |
| MACKAMINE LO | 4.5 | 4.5 |
| Glycerin | 2.5 | 2.5 |
| GLUCAMATE DOE 120 | 3.0 | 5.0 |
| NaCl | 1.0 | — |
| Citric Acid (25%) | 1.5 | 1.0 |
| MACKERNIUM SFES | — | 3.2 |
| Water | q.s. | q.s. |

Both Samples 3A and 3B were clear, phase stable, and had a consumer acceptable viscosity.

EXAMPLE 4

This example summarizes the exceptional antibacterial efficacy of a composition of the present invention. Antibacterial efficacy was assessed by time kill tests. The compositions exhibit an antibacterial efficacy considerably superior to that provided by present-day commercial antibacterial compositions. Table 1 summarizes the log reductions measured in time kill tests at contact times of 30 seconds and 1 minute.

TABLE 1

| | Log Reduction | | | |
|---|---|---|---|---|
| | S. aureus | | E. coli | |
| Sample | 30 sec | 1 min | 30 sec | 1 min |
| 1A (pH-5.99) | >4.95 | >4.95 | >5.00 | >5.00 |
| 1B | 3.94 | 4.75 | >4.85 | 4.70 |
| 1C | 4.52 | 4.85 | >4.85 | >4.85 |
| 1D | 3.64 | 4.85 | >4.85 | >4.85 |
| 1E | 3.39 | 4.06 | >5.00 | >5.00 |
| 2A | 3.50 | 4.23 | >4.62 | >4.62 |
| 2B | 3.38 | 3.48 | >4.62 | >4.62 |
| 3A | 3.43 | 4.06 | 4.88 | 4.68 |
| 3B (pH-5.82) | 1.6 | 2.23 | >5.0 | >5.0 |

Preferred compositions of the present invention contain, by total weight of the composition:
about 0.05 to about 5% of an antibacterial agent selected from the group consisting of benzethonium chloride, o-phenylphenol, triclosan, benzalkonium chloride, and mixtures thereof;
about 1 to about 15% of a ($C_8$–$C_{22}$)alkamine oxide, preferably comprising lauramine oxide;
about 1 to about 10% of a cosurfactant selected from the group consisting of an alkyl polyglucose, preferably comprising decyl polyglucose, cocamidopropyl betaine MEA chloride, stearyl dimethyl ethylhexyl ammonium methosulfate, and mixtures thereof;
0 to about 5% glycerin; and
0 to about 3% of a polymeric thickener selected from the group consisting of PEG-120 methyl glucose dioleate, hydroxyethyl ethylcellulose, sunflower seed amidopropyl ethyldimonium ethylsulfate, PPG-14 palmeth-60 alkyl, ceteareth-60 myristyl glycol, and mixtures thereof; and having a pH of about 5.5 to about 7.5, preferably about 6 to about 7.3.

EXAMPLE 5

This example illustrates the relationship between pH and antibacterial activity of 2% active aqueous lauramine oxide solutions. The efficacy data are log reductions after 30 seconds against the indicated bacteria.

| pH | S. aureus | E. coli |
|---|---|---|
| 4.93 | 2.11 | >5.32 |
| 5.50 | >4.38 | >4.70 |
| 6.02 | >4.39 | >4.70 |
| 6.5 | >4.39 | >4.70 |
| 7.0 | >4.39 | >5.32 |
| 7.53 | >4.39 | 0.88 |
| 8.94 | 4.33 | 0.27 |
| 10.14 | 3.75 | 0.11 |

This example shows that lauramine oxide exhibits a high, broad-spectrum efficacy at a 2% active concentration within a pH range of about 5.5 to about 7.5.

EXAMPLE 6

This example illustrates the relationship between pH and antibacterial efficacy for an unthickened composition of the present invention.

| Material | A | B | C |
|---|---|---|---|
| Water | qs | qs | qs |
| Decyl polyglucose | 1.44 | 1.44 | 1.44 |
| BZC | 0.25 | 0.25 | 0.25 |
| Glycerin | 2.5 | 2.5 | 2.5 |
| Lauramine oxide | 2.25 | 2.25 | 2.25 |
| Citric acid[1] | qs | qs | qs |
| pH | 6.0 | 6.5 | 7.0 |

[1]added in a sufficient amount, typically 0–0.5% by weight of the composition, to adjust the pH to the desired value.

Samples 6A-6C were tested for time kill at 50% dilution. The results are summarized in the following table.

| | | Log Reduction at 30 seconds | |
|---|---|---|---|
| Sample | pH | S. aureus | E. coli |
| 6A | 6.0 | 3.37 | >4.86 |
| 6B | 6.5 | 4.41 | >4.86 |
| 6C | 7.0 | 4.51 | 1.21 |

This example shows that an unthickened composition of the present invention exhibits a more effective broad spectrum antibacterial activity at pH 6 and 6.5 than at pH 7.

EXAMPLE 7

This example illustrates that a composition of the present invention exhibits an excellent broad-spectrum activity at pH 7.12.

| Material | Composition wt. % |
|---|---|
| Water | 77.96 |
| Decyl polyglucose | 1.48 |
| BZC | 0.25 |
| Glycerin | 2.5 |
| Lauramine oxide | 2.25 |
| Citric acid | 0.075 |

-continued

| Material | Composition wt. % |
|---|---|
| MONTALAINE C-40 | 2.3 |
| Hydroxymethyl cellulose | 1.25 |
| Fragrance | 0.3 |
| Sodium hydroxide | 0.05 |
| FD&C Yellow 5 (dye) | 0.0062 |
| FD&C Red 4 (dye) | 0.0033 |
| DMDM Hydantoin (preservative) | 0.22 |

The composition of Example 7 was tested for time kill at 50% dilution against *S. aureus, E. coli,* and *K. Pneum.,* and achieved respective log reduction of >4.69, >4.74, and >4.43, respectively, after 30 seconds.

EXAMPLE 8

This example illustrates that a composition having a pH outside of the preferred 6 to 7.3 pH range exhibits a good, but reduced, level of broad-spectrum antibacterial efficacy. The following compositions were prepared and tested for time-kill at 50% dilution against the bacteria indicated in the following table.

| | Composition wt. % | | | | | |
|---|---|---|---|---|---|---|
| Ingredient | A | B | C | D | E | F |
| Water | qs | qs | qs | qs | qs | qs |
| PLANTAREN 2000 N | 1.5 | 3.25 | 1.5 | 1.5 | — | 1.5 |
| BZC | 0.25 | 0.25 | 0.25 | — | — | 0.25 |
| TCS | — | — | — | 0.2 | 0.25 | — |
| Glycerin | 2.5 | 2.5 | 2.5 | 2.5 | 2.5 | 2.5 |
| MACKAMINE LO | 2.25 | 5.0 | 2.25 | 2.25 | 5.0 | 2.25 |
| Citric acid | 1.03 | 0.5 | 0.2 | 0.2 | 0.65 | 0.175 |
| MONTELAINE C-40 | — | — | 2.3 | 2.3 | — | — |
| ARQUAD HTL8-MS | 3.2 | — | 4.2 | 4.2 | — | — |
| MACKERNIUM DY-83 | — | — | — | — | 3.2 | 3.2 |
| STANDAMOX CAW[1] | 0.54 | — | — | — | — | — |
| ELFACOS GT282S | 2.55 | — | — | — | — | — |
| ELFACOS T212 | — | — | — | — | — | 2.55 |
| DOWICIDE 1 | — | — | — | — | — | 0.25 |
| GLUCAMATE DOE-120 | — | 2.55 | 3.06 | 3.06 | 5.0 | — |
| Sodium Chloride | 1.05 | 1.0 | 0.51 | 0.51 | — | 0.1 |
| pH | 5.66 | 5.67 | 5.84 | 5.84 | 5.86 | 5.74 |

[1]STANDAMOX CAW is cocamidopropyl amine oxide, 30% active, available from Cognis Care Chemicals.

| | Log Reduction at 30 seconds | |
|---|---|---|
| Composition | S. aureus | E. coil |
| 8A | 0.53 | >4.14 |
| 8B | 2.27 | 4.55 |
| 8C | 2.01 | >4.84 |
| 8D | 1.45 | >4.84 |
| 8E | 1.8 | >5.0 |
| 8F | 0.69 | >4.61 |

Example 8 clearly demonstrates the role pH plays in the efficacy of compositions of the invention.

EXAMPLE 9

The following two compositions of the present invention contain a combination of amine oxides. The compositions were prepared by admixing procedures well known to persons skilled in the art. Stearamine oxide is available as Mackamine SO (about 25% active amine oxide), from McIntyre Chemicals, University Park, Ill.

| Chemical | Composition (wt. %) | |
| --- | --- | --- |
|  | A | B |
| Benzethonium Chloride | 0.25 | 0.25 |
| Deionized Water | 83.55 | 84.48 |
| Decyl Polyglucose | 2.5 | 2.5 |
| Glycerin | 2.0 | 2.0 |
| Lauramine Oxide | 5.0 | 3.75 |
| Stearamine Oxide | 2.5 | 3.75 |
| Glyceryl Laurate | 0.5 | 0.5 |
| Sunflower amindopropyl ethonium sulfate | 1.0 | 1.1 |
| PEG 120 methyl gluceth dioleate | 1.5 | 1.5 |
| Fragrane | 0.2 | — |
| Dye Solution | 0.7 | — |
| Citric acid | 0.30 | 0.17 |

Compositions 9A and 9B had good viscosity and good lather properties.

The data presented in the above examples and tables show that a present antibacterial composition can exhibit a log reduction of at least about 2 (after 30 seconds) or at least about 3 (after 60 seconds) vs. S. aureus, or of at least about 2.5 (after 30 seconds) or at least about 3.5 (after 60 seconds) vs. E. coli.

The antibacterial compositions of the present invention have several practical end uses, including hand cleansers, mouthwashes, surgical scrubs, body splashes, hand sanitizer gels, and similar personal care products. Additional types of compositions include foamed compositions, such as creams, mousses, and the like, and compositions containing organic and inorganic filler materials, such as emulsions, lotions, creams, pastes, and the like. The compositions further can be used as an antibacterial cleanser for hard surfaces, for example, sinks and countertops in hospitals, food service areas, and meat processing plants. The present antibacterial compositions can be manufactured as dilute ready-to-use compositions, or as concentrates that are diluted prior to use.

The compositions also can be incorporated into a web material to provide an antibacterial wiping article. The wiping article can be used to clean and sanitize skin or inanimate surfaces.

The present antimicrobial compositions provide the advantages of a broad spectrum kill of Gram positive and Gram negative bacteria in short contact times. The short contact time for a substantial log reduction of bacteria is important in view of the typical 15 to 60 second time frame used to cleanse and sanitize the skin and inanimate surfaces.

Obviously, many modifications and variations of the invention as hereinbefore set forth can be made without departing from the spirit and scope thereof, and, therefore, only such limitations should be imposed as are indicated by the appended claims.

What is claimed is:

1. An antimicrobial composition comprising:
   (a) about 0.05% to about 5%, by weight, of a phenolic antibacterial agent;
   (b) about 1% to about 15%, by weight, of an alkamine oxide surfactant;
   (c) about 1% to about 10%, by weight, of (i) a nonionic cosurfactant selected from the group consisting of an ethoxylated alkylphenol, an ethoxylated fatty alcohol, a propoxylated fatty alcohol, an alkyl polyglucoside, a polyethylene glycol ether of sorbitol, an ethylene oxide-propylene oxide block copolymer, an ethoxylated ester of a fatty ($C_8$–$C_{14}$) acid, a condensation product of ethylene oxide with a long chain amine or amide, and mixtures thereof, (ii) a cationic cosurfactant, or (iii) a mixture thereof;
   (d) 0% to about 5%, by weight, of a polymeric thickener; and
   (e) water,
   wherein the antibacterial composition has a pH of about 5.5 to about 7.5, and is free of an anionic surfactant.

2. The composition of claim 1 having a log reduction against Gram positive bacteria of at least 2 after 30 seconds of contact, as measured against S. aureus, and a log reduction against Gram negative bacteria of at least 2.5 after 30 seconds of contact, as measured against E. coli.

3. The composition of claim 1 comprising about 0.1% to about 3%, by weight, of the phenolic antibacterial agent.

4. The composition of claim 1 wherein the phenolic antibacterial agent is selected from the group consisting of:
   (a) a 2-hydroxydiphenyl compound having the structure

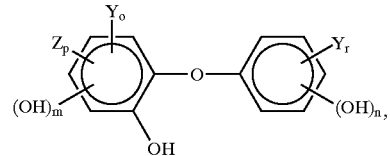

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1;

(b) a phenol derivative having the structure

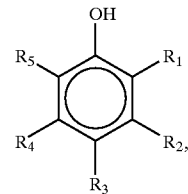

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl; and $R_5$ is hydro or nitro;

(c) a diphenyl compound having the structure

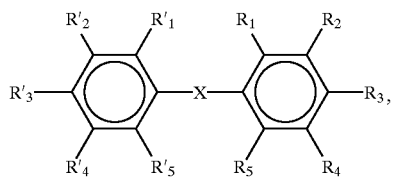

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo; and
   (d) mixtures thereof.

5. The composition of claim 1 wherein the phenolic antibacterial agent is selected from the group consisting of triclosan, 2,2'-dihydroxy-5,5'-dibromodiphenyl ether, p-chloro-m-xylenol, ortho-phenylphenol, and mixtures thereof.

6. The composition of claim 1 wherein the alkamine oxide surfactant is present in an amount of about 1.5% to about 10%, by weight of the composition.

7. The composition of claim 1 wherein the alkamine oxide is selected from the group consisting of:

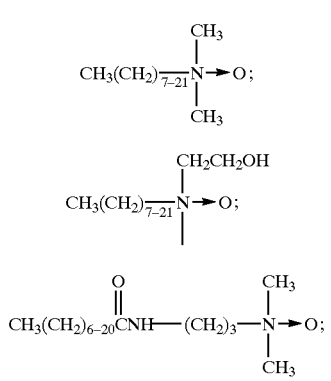

(d) an alkylmorpholine oxide, wherein the alkyl group contains 8 to 22 carbon atoms, and
(e) mixtures thereof.

8. The composition of claim 1 wherein the alkamine oxide is selected from the group consisting of lauryl dimethyl amine oxide, myristyl dimethyl amine oxide, dimethyl cocoamine oxide, dimethyl (hydrogenated tallow)amine oxide, myristyl/palmityl dimethyl amine oxide, myristyl/lauryl dimethyl amine oxide, cetyl dimethyl amine oxide, stearyl dimethyl amine oxide, myristyl/cetyl dimethyl amine oxide, bis(2-hydroxyethyl)cocoamine oxide, bis(2-hydroxyethyl)tallow amine oxide, bis(2-hydroxyethyl) stearylamine oxide, cocoamidopropyl dimethyl amine oxide, tallowamidopropyl dimethyl amine oxide, decyl dimethylamine oxide, lauryl dimethylamine oxide, stearyl dimethylamine oxide, oleyl dimethylamine oxide, coco dihydroxyethylamine oxide, cetyl dihydroxyethylamine oxide, oleyl dihydroxyethylamine oxide, cocamine oxide, cocamidopropylamine oxide, lauramidopropylamine oxide, oleamine oxide, oleamidopropylamine oxide, wheat germamidopropylamine oxide, isostearamidopropylamine oxide, stearamine oxide, stearamidopropylamine oxide, cocomorpholine oxide, decylamine oxide, dihydroxyethyl $C_8$–$C_{10}$alkoxypropylamine oxide, dihydroxyethyl $C_9$–$C_{11}$alkoxypropylamine oxide, dihydroxyethyl $C_{12}$–$C_{15}$alkoxypropylamine oxide, dihydroxyethyl cocamine oxide, dihydroxyethyl stearamine oxide, dihydroxyethyl tallowamine oxide, hydrogenated tallow amine oxide, hydroxyethyl hydroxypropyl$C_{12}$–$C_{15}$-alkoxypropylamine oxide, isostearamidopropyl morpholine oxide, myristamidopropylamine oxide, myristamine oxide, palmitamidopropylamine oxide, palmitamine oxide, PEG-3 lauramine oxide, tallow amidopropylamine oxide, tallow amine oxide, undecylenamidopropylamine oxide, and mixtures thereof.

9. The composition of claim 1 wherein the alkamine oxide is selected from the group consisting of lauramine oxide, myristamine oxide, cocamine oxide, cetamine oxide, stearamine oxide, oleamine oxide, stearqmine oxide, oleamine oxide, and mixtures thereof.

10. The composition of claim 1 wherein the cosurfactant is present in an amount of about 1.5% to about 8%, by weight of the composition.

11. The composition of claim 1 wherein the nonionic cosurfactant is selected from the group consisting of $C_{11}$–$C_{15}$pareth-20, ceteth-12, dodoxynol-12, laureth-15, polysorbate 20, an ethoxylated nonylphenol, an ethoxylated octylphenol, an ethoxylated dodecylphenol, an ethoxylated fatty ($C_6$–$C_{18}$) alcohol containing 9 to 50 ethylene oxide moieties, glycereth-12, glycereth-26, trideceth-9, trideceth-10, trideceth-11, trideceth-12, trideceth-15, sorbeth-20, dodoxynol-9, dodoxynol-12, chlorodeceth-14, chloeth-10, dihydrocholeth-15, isoceteth-10, isoceteth-20, isoceteth-30, isolaureth-10, isosteareth-10, isosteareth-12, isosteareth-20, laneth-10, laneth-15, laneth-16, laneth-20, oleth-9, oleth-10, oleth-12, oleth-15, oleth-16, oleth-20, steareth-10, steareth-11, steareth-13, steareth-15, steareth-16, steareth-20, talloweth-6, laureth-9, laureth-10, laureth-11, laureth-12, laureth-13, laureth-14, laureth-15, laureth-20, and mixtures thereof.

12. The composition of claim 1 wherein the cosurfactant is selected from the group consisting of decyl polyglucose, lauryl polyglucose, sunflower seed amidopropylethyldimonium ethosulfate, and a mixture thereof.

13. The composition of claim 1 wherein the composition is free of a zwitterionic surfactant.

14. The composition of claim 1 wherein the polymeric thickener is present in an amount of about 0.25% to about 4%, by weight of the composition.

15. The composition of claim 1 having a viscosity of about 0.1 to about 10,000 centipoise.

16. The composition of claim 1 wherein the polymeric thickener is selected from the group consisting of a cellulose thickener, a hydrophobically modified polyethylene glycol, a hydrophobically modified polypropylene glycol, a hydrophobic alkoxylated alcohol, and mixtures thereof.

17. The composition of claim 1 wherein the thickener is selected from the group consisting of hydroxyethylcellulose, hydroxyethyl ethylcellulose, hydroxybutyl methylcellulose, hydroxypropyl methylcellulose, hydroxypropylcellulose, polyquaternium 10, polyquaternium 4, hydroxypropyl methylcellulose, PEG-120 methyl glucose dioleate, PPG-14 palmeth-60 alkyl, ceteareth-60 myristyl glycol, methoxy PEG-22/dodecyl glycol copolymer, methyl gluceth-20, PEG-20 castor oil, PEG-25 castor oil, PEG-30 castor oil, PEG-36 castor oil, PEG-40 castor oil, PEG-50 castor oil, PEG-60 castor oil, PEG-100 castor oil, PEG-45/dodecyl glycol copolymer, PEG-20 hydrogenated castor oil, PEG-25 hydrogenated castor oil, PEG-30 hydrogenated castor oil, PEG-40 hydrogenated castor oil, PEG-50 hydrogenated castor oil, PEG-60 hydrogenated castor oil, PEG-80 hydrogenated castor oil, PEG-100 hydrogenated castor oil, PPG-20 lanolin alcohol ether, PPG-30 lanolin alcohol ether, PPG-25-laureth-25, PPG-20 oleyl ether, PPG-23 oleyl ether, PPG-30 oleyl ether, PPG-37 oleyl ether, PPG-50 oleyl ether, PPG-20 methyl glucose ether, PPG-20 methyl glucose ether acetate, PEG-10 lanolin, PEG-20 lanolin, PEG-24 lanolin, PEG-27 lanolin, PEG-30 lanolin, PEG-40 lanolin, PEG-50 lanolin, PEG-60 lanolin, PEG-75 lanolin, PEG-85 lanolin, PEG-100 lanolin, PEG-75 lanolin oil, PEG-75 lanolin wax, PEG-20 methyl glucose sesquistereate, PEG-20-PPG-10 glyceryl stearate, PEG-25 propylene glycol stearate, PEG-75 propylene glycol stearate, PEG-120 propylene glycol stearate, PEG-25 soya sterol, PEG-40 soya sterol, talloweth-60 myristyl glycol, and mixtures thereof.

18. The composition of claim 1 further comprising one or more of a hydric solvent, a hydrotrope, a pH adjuster, a skin conditioner, an oil, and an emollient, each in an amount of 5% or less by weight of the composition.

19. The composition of claim 1 having a pH of about 6 to about 7.3.

20. An antimicrobial composition comprising:
(a) about 0.05% to about 5%, by weight, of a quaternary ammonium antibacterial agent;
(b) about 1% to about 15%, by weight, of a ($C_8$–$C_{22}$) alkamine oxide;
(c) about 1% to about 10%, by weight, of a cosurfactant selected from the group consisting of an alkyl polyglucose, cocamidopropyl betaine MEA chloride, polyquaternium 10, stearyl dimethyl ethylhexyl ammonium methosulfate, sunflower seed amidopropyl ethyldimonium ethylsulfate, and mixtures thereof;
(d) 0 to about 5%, by weight, glycerin; and
(e) 0 to about 3%, by weight, of a polymeric thickener; and having a pH of about 6 to about 7.3.

21. A method of reducing a bacteria population on a surface comprising contacting the surface with a composition of claim 20 for a sufficient time to provide a log reduction of bacteria of at least 2, then rinsing the composition from the surface.

22. The method of claim 21 wherein the surface is a skin of a mammal.

23. The method of claim 21 wherein the surface is a hard, inanimate surface.

24. The method of claim 21 wherein the composition contacts the surface for 30 seconds to achieve a log reduction of at least 2 against *S. aureus*.

25. The method of claim 21 wherein the composition contacts the surface for 60 seconds to achieve a log reduction of at least 3 against *S. aureus*.

26. The method of claim 21 wherein the composition contacts the surface for 30 seconds to achieve a log reduction of at least 2.5 against *E. coil*.

27. The method of claim 21 wherein the composition contacts the surface for 60 seconds to achieve a log reduction of at least 3.75 against *E. coli*.

28. The composition of claim 20 comprising about 0.2% to about 2% by weight, of the quaternary ammonium antibacterial agent.

29. The composition of claim 20 wherein the quaternary ammonium antibacterial agent has a structure:

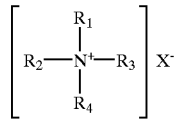

wherein $R_1$ is an alkyl, aryl, or alkaryl substituent containing 6 to 26 carbon atoms, $R_2$, $R_3$, and $R_4$, independently, are substituents containing no more than twelve carbon atoms, and X is an anion selected from the group consisting of halo, methosulfate, ethosulfate, and p-toluenesulfonyl.

30. The composition of claim 29 wherein $R_1$ is selected from the group consisting of $C_6$–$C_{26}$alkyl, $C_6$–$C_{26}$alkoxyaryl, $C_6$–$C_{26}$alkaryl, halogen-substituted $C_6$–$C_{26}$alkaryl, and $C_6$–$C_{26}$alkylphenoxyalkyl.

31. The composition of claim 29 wherein $R_2$, $R_3$, and $R_4$, independently, contain one or more amide, ether, or ester linkage.

32. The composition of claim 20 wherein the quaternary ammonium antibacterial agent has a structure:

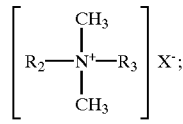

wherein $R_2$ and $R_3$, independently, are $C_8$–$C_{12}$alkyl, or $R_2$ is $C_{12}$–$C_{16}$alkyl, $C_8$–$C_{18}$alkylethoxy, or $C_8$–$C_{18}$alkylphenylethoxy, and $R_3$ is benzyl, and X is halo, methosulfate, ethosulfate, or p-toluenesulfonate.

33. The composition of claim 20 wherein the quaternary ammonium antibacterial agent is selected from the group consisting of an alkyl ammonium halide, an alkyl aryl ammonium halide, an N-alkyl pyridinium halide, and mixtures thereof.

34. The composition of claim 20 wherein the quaternary ammonium antibacterial agent is selected from the group consisting of cetyl trimethyl ammonium bromide, octadecyl dimethyl benzyl ammonium bromide, N-cetyl pyridinium bromide, octylphenoxyethoxy ethyl dimethyl benzyl ammonium chloride, N-(laurylcoco-aminoformylmethyl) pyridinium chloride, lauryloxyphenyl-trimethyl ammonium chloride, cetylaminophenyl trimethyl ammonium methosulfate, dodecylphenyl trimethyl ammonium methosulfate, dodecylbenzyl trimethyl ammonium chloride, chlorinated dodecylbenzyl trimethyl ammonium chloride, dioctyl dimethyl ammonium chloride, benzalkonium chloride, myristyl dimethylbenzyl ammonium chloride, methyl dodecyl xylene-bis-trimethyl ammonium chloride, benzethonium chloride, a 2-butenyl dimethyl ammonium chloride polymer, behenalkonium chloride, cetalkonium chloride, cetarylalkonium bromide, cetrimonium tosylate, cetylpyridinium chloride, lauralkonium bromide, lauralkonium chloride, lapyrium chloride, lauryl pyridinium chloride, myristalkonium chloride, olealkonium chloride, isostearyl ethyldimonium chloride, and mixtures thereof.

35. The composition of claim 20 wherein the ($C_8$–$C_{22}$) alkamine oxide is present in an amount of about 2% to about 8%, by weight of the composition.

36. The composition of claim 20 wherein the cosurfactant is present in an amount of about 2% to about 6%, by weight of the composition.

37. The composition of claim 20 wherein the polymeric thickener is present in an amount of about 0.5% to about 3%, by weight of the composition, and the composition has a viscosity of about 500 to about 5,000 centipoise.

* * * * *

UNITED STATES PATENT AND TRADEMARK OFFICE
CERTIFICATE OF CORRECTION

PATENT NO.     : 6,616,922 B2                    Page 1 of 1
DATED          : September 9, 2003
INVENTOR(S)    : Timothy J. Taylor et al.

It is certified that error appears in the above-identified patent and that said Letters Patent is hereby corrected as shown below:

Column 24,
Line 34, "0or" should be -- 0 or --

Column 25,
Line 19,

" 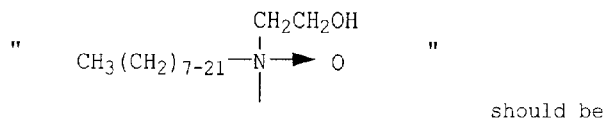 "

should be

-- 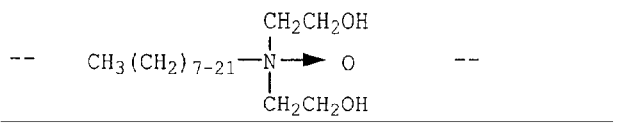 --

Line 54, "$C_{15}$-alkoxypropylamine" should be -- $C_{15}$alioxyproplyamine --

Column 27,
Line 32, "*E coil.*" should be -- *E coli.* --

Column 28,
Line 29, "laurylcoco-aminoformylmethyl" should be -- laurylcocoaminoformylmethyl --

Signed and Sealed this

Thirteenth Day of April, 2004

JON W. DUDAS
*Acting Director of the United States Patent and Trademark Office*